(12) United States Patent
Wang et al.

(10) Patent No.: US 11,341,938 B2
(45) Date of Patent: May 24, 2022

(54) SYSTEMS, METHODS, AND APPARATUSES FOR DISPLAY

(71) Applicant: SHANGHAI UNITED IMAGING HEALTHCARE CO., LTD., Shanghai (CN)

(72) Inventors: Mingchao Wang, Shanghai (CN); Bo Song, Shanghai (CN); Yusheng Yin, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/107,857

(22) Filed: Nov. 30, 2020

(65) Prior Publication Data
US 2021/0166662 A1 Jun. 3, 2021

(30) Foreign Application Priority Data

Nov. 29, 2019 (CN) .......................... 201911202040.3
Dec. 23, 2019 (CN) .......................... 201911336888.5

(51) Int. Cl.
*G09G 5/37* (2006.01)
*G09G 5/02* (2006.01)
(Continued)

(52) U.S. Cl.
CPC ............. *G09G 5/377* (2013.01); *A61B 6/035* (2013.01); *A61B 6/4435* (2013.01); *G09G 5/02* (2013.01);
(Continued)

(58) Field of Classification Search
CPC combination set(s) only.
See application file for complete search history.

(56) References Cited

U.S. PATENT DOCUMENTS

2013/0207948 A1\* 8/2013 Na .......................... G09G 3/003
345/207
2017/0132970 A1 5/2017 Tang
(Continued)

FOREIGN PATENT DOCUMENTS

CN 2752815 Y 1/2006
CN 102708758 A 10/2012
(Continued)

OTHER PUBLICATIONS

First Office Action in Chinese Application No. 201911336888.5 dated Apr. 2, 2021, 20 pages.

*Primary Examiner* — Wesner Sajous
(74) *Attorney, Agent, or Firm* — Metis IP LLC

(57) ABSTRACT

The present disclosure provides a display apparatus. The display apparatus may include a display panel including a frame area and a display area; a display component configured to display a content including a target portion and a background portion on the display area; an image acquisition device configured to acquire an image of the display panel, wherein the image includes a representation of at least one portion of the frame area and at least one portion of the display area; and a control device configured to control the display component to adjust the background portion of the content displayed on the display area according to the image of the display panel.

20 Claims, 11 Drawing Sheets

(51) Int. Cl.
*G09G 5/10* (2006.01)
*A61B 6/03* (2006.01)
*G09G 5/377* (2006.01)
*A61B 6/00* (2006.01)

(52) U.S. Cl.
CPC ....... *G09G 5/10* (2013.01); *G09G 2320/0626* (2013.01); *G09G 2320/0666* (2013.01); *G09G 2380/08* (2013.01)

(56) References Cited

U.S. PATENT DOCUMENTS

| | | | |
|---|---|---|---|
| 2017/0168124 A1* | 6/2017 | Ueda | H04N 9/3185 |
| 2017/0322271 A1* | 11/2017 | Gulaka | G01R 33/283 |
| 2018/0115734 A1 | 4/2018 | Whang et al. | |
| 2018/0165052 A1* | 6/2018 | Kim | G06F 3/14 |
| 2018/0247613 A1 | 8/2018 | Lee et al. | |
| 2018/0267307 A1* | 9/2018 | Yoshida | G02F 1/13318 |
| 2019/0287490 A1 | 9/2019 | Lee et al. | |

FOREIGN PATENT DOCUMENTS

| | | |
|---|---|---|
| CN | 103295481 A | 9/2013 |
| CN | 106409167 A | 2/2017 |
| CN | 107093395 A | 8/2017 |
| CN | 104639748 B | 10/2017 |
| CN | 107680496 A | 2/2018 |
| CN | 108415681 A | 8/2018 |

\* cited by examiner

800

```
┌─────────────────────────────────────────────┐
│ Obtaining an image of a display panel of a  │
│ display apparatus, the display panel        │
│ including a display area and a frame area,  │
│ a content including a target portion and a  │──── 810
│ background portion being displayed on the   │
│ display area, the image of the display      │
│ panel including a representation of at      │
│ least one portion of the frame area and at  │
│ least one portion of the display area       │
└─────────────────────────────────────────────┘
                      │
                      ▼
┌─────────────────────────────────────────────┐
│ Determining a reference value of a          │
│ parameter of the frame area represented in  │──── 820
│ the image of the display panel              │
└─────────────────────────────────────────────┘
                      │
                      ▼
┌─────────────────────────────────────────────┐
│ Determining a value of the parameter of the │──── 830
│ background portion represented in the image │
└─────────────────────────────────────────────┘
                      │
                      ▼
┌─────────────────────────────────────────────┐
│ Adjusting one or more display parameters of │
│ the background portion according to the     │
│ value of the parameter of the background    │──── 840
│ portion and the reference value of the      │
│ parameter of the frame area                 │
└─────────────────────────────────────────────┘
```

FIG. 8

SYSTEMS, METHODS, AND APPARATUSES FOR DISPLAY

CROSS-REFERENCE TO RELATED APPLICATIONS

This application claims priority of Chinese Patent Application No. 201911336888.5, filed on Dec. 23, 2019, and Chinese Patent Application No. 201911202040.3, filed on Nov. 29, 2019, the contents of each of which are hereby incorporated by reference.

TECHNICAL HELD

The present disclosure generally relates to a display apparatus, and more particularly, to a display apparatus for borderless display.

BACKGROUND

With the development of light-emitting diode (LED) technology; display apparatuses are widely used in various places, such as stadiums, exhibition halls, performance places, conference venues, etc. Generally, a display apparatus includes a substantial bezel (or border) around the display apparatus. When the display apparatus displays a content, a user can see an obvious boundary between the content and the bezel. Thus, it is desirable to develop a display apparatus without an obvious boundary between a content and a bezel of the display apparatus when the content is displayed to improve the user viewing experience.

SUMMARY

According to an aspect of the present disclosure, a display apparatus is provided. The display apparatus may include a display panel including a frame area and a display area; a display component configured to display a content including a target portion and a background portion on the display area; an image acquisition device configured to acquire an image of the display panel, wherein the image includes a representation of at least one portion of the frame area and at least one portion of the display area; and a control device configured to control the display component to adjust the background portion of the content displayed on the display area according to the image of the display panel.

In some embodiments, to adjust the background portion of the content displayed on the display area according to the image of the display panel, the control device may be further configured to determine a reference value of an image parameter of the frame area represented in the image of the display panel. The control device may determine a value of the image parameter of the background portion represented in the image. The control device may control the display component to adjust one or more display parameters of the background portion according to the value of the image parameter of the background portion and the reference value of the image parameter of the frame area.

In some embodiments, after adjusting the one or more display parameters of the background portion, a difference between the value of the image parameter of the background portion and the reference value of the image parameter of the frame area may be smaller than a threshold.

In some embodiments, after adjusting the one or more display parameters of the background portion, the value of the image parameter of the background portion may be the same as the reference value of the image parameter of the frame area.

In some embodiments, the control device may be further configured to determine a value of the image parameter of the target portion represented in the image, and adjust one or more display parameters of the target potion based on the value of the image parameter of the target portion and the reference value of the image parameter of the frame area.

In some embodiments, the image parameter may include at least one of a color parameter or a brightness parameter.

In some embodiments, the display area of the display panel may be made of a transparent material or a semi-transparent material.

In some embodiments, the display component may include a light emitting element, the light emitting element includes at least one of a thin film transistor liquid crystal, an organic light-emitting diode (OLEO), a LED dot matrix, a micro light emitting diode (micro LED) a plasma light emitting element, or a projector.

In some embodiments, the display component may be located at a first side of the display panel or is spaced apart from the display panel. The image acquisition device may be located at the first side or a second side of the display panel. A field of view (FOV) of the image acquisition device may cover the at least one portion of the frame area and the at least one portion of the display area.

In some embodiments, the display apparatus may be arranged in a medical device including a gantry with a bore. The display panel may include at least a portion of an inner surface of the gantry.

In some embodiments, the display component may include one or more light sources configured to provide lighting for the bore; and one or more diffraction components configured to generate the content based on one or more light beams generated by the one or more light sources and display the content on the inner surface of the gantry, each diffraction component corresponding to one light source.

According to another aspect of the present disclosure, a method is provided. The method may include obtaining an image of a display panel of a display apparatus, the display panel including a display area and a frame area, a content including a target portion and a background portion being displayed on the display area, the image of the display panel including a representation of at least one portion of the frame area and at least one portion of the display area; determining a reference value of an image parameter of the frame area represented in the image of the display panel; determining a value of the image parameter of the background portion represented in the image; and adjusting one or more display parameters of the background portion according to the value of the image parameter of the background portion and the reference value of the image parameter of the frame area.

According to yet another aspect of the present disclosure, a medical device is provided. The medical device may include a gantry including a bore configured to accommodate an object; and a lighting device including one or more light sources and one or more display apparatuses, wherein the one or more light sources are configured to provide lighting for the bore; and the one or more display apparatuses are configured to display a content on an inner surface of the gantry.

In some embodiments, the inner surface of the gantry may include a frame area and a display area. The display apparatus may include a display component configured to display a content including a target portion and a background portion on the display area; an image acquisition device configured to acquire an image of the inner surface of the gantry, wherein the image includes at least a portion of the frame area and at least a portion of the display area; and a control device configured to control the display component to adjust the background portion of the content displayed on the display area according to the image of the inner surface of the gantry.

In some embodiments, one of the one or more light sources may be arranged at an end of a sagittal axial of the gantry; and one of the one or more display apparatuses may include a diffraction component configured to generate the content based on a light beam generated by the one of the one or more light sources and display the content on the inner surface of the gantry.

In some embodiments, one of the one or more light sources may include at least one of a laser light or a LED light, and the diffraction component may include a grating element.

In some embodiments, the lighting device may further include a LED strip, the LED strip being set on the end of the sagittal axial of the gantry where the one of the one or more light sources is located.

In some embodiments, a brightness intensity of the LED strip may change at a first frequency, and a brightness intensity of at least one of the one or more light sources may change at a second frequency, wherein the first frequency is same as the second frequency.

In some embodiments, the lighting device may further include a support component configured to support the one of the one or more light sources and the diffraction component.

In some embodiments, the support component may have a tube. The diffraction component may be arranged on an end of the tube, and one of the light sources may be movably arranged in the support component to adjust a focal length of the one of the light sources.

In some embodiments, the diffraction component may include a pattern configured to provide the content for display, and the pattern may include at least one of a geometric pattern, an animal pattern, a constellation pattern, a letter, or a number.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 8 is a flowchart illustrating an exemplary process for borderless display according to some embodiments of the present disclosure;

DETAILED DESCRIPTION

Figure 1:
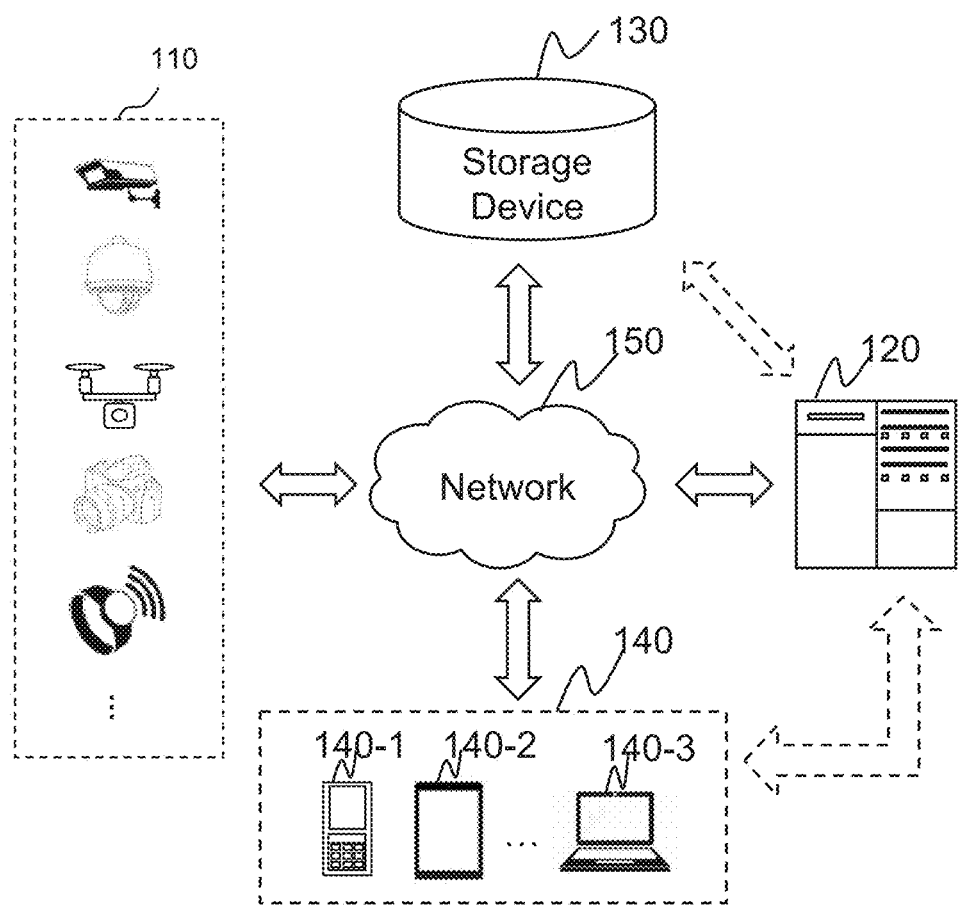
FIG. 1 is a schematic diagram illustrating an exemplary display system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or maybe invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, section or assembly of different levels in ascending order. However, the terms may be displaced by another expression if they achieve the same purpose.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," "disposed," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent"). In some embodiments, engine, module, or block is referred to as being "on," "connected to," or "coupled to," another unit, engine, module, or block, it may communicate with the other unit, engine, module, or block. As used herein, the term "and/or" includes any and all combinations of one or more of the associated listed items.

It should also be understood that terms such as "top," "bottom," "upper," "lower," "vertical," "lateral," "above," "below," "upward(s)," "downward(s)," "left-hand side," "right-hand side," "left," "right," "horizontal," and other such spatial reference terms are used in a relative sense to describe the positions or orientations of certain surfaces/parts/components of a device with respect to other such features of the device when the device is in a normal operating position and may change if the position or orientation of the device changes.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems, methods, and display apparatuses for borderless display. The display apparatus may include a display panel, a display component, an image acquisition device, and a control device. The display panel may include a frame area and a display area. The display component may be configured to display a content including a target portion and a background portion on the display area. The image acquisition device may be configured to acquire an image of the display panel, wherein the image includes a representation of at least one portion of the frame area and at least one portion of the display area. The control device may be configured to control the display component to adjust the background portion of the content displayed on the display area according to the image of the display panel. According to some embodiments of the present disclosure, one or more display parameters of the background portion may be adjusted so that a difference between a value of an image parameter (e.g., a color parameter and/or a brightness parameter) of the background portion and a reference value of the image parameter of the frame area is smaller than a threshold. In some embodiments, the value of the image parameter of the background portion and the reference value of the image parameter of the frame area may be adjusted to be the same. In such cases, the display apparatus may present a visual effect of borderless (or substantially borderless) display, i.e., without an obvious boundary between the content and the frame area when the content is displayed, thereby improving the user viewing experience.

Another aspect of the present disclosure relates to medical devices. The medical device may include a gantry including a bore configured to accommodate an object. The medical device may further include one or more light sources and one or more display apparatuses. The one or more light sources may be configured to provide lighting for the bore. The one or more display apparatuses may be configured to display a content on an inner surface of the gantry. Accordingly, when an object (e.g., a child, a patient) is located in the bore for medical treatment and/or imaging; the bore may be illuminated by the lighting sources and a content (e.g. a pattern, a video) may be displayed on the inner surface of the gantry. In such cases, it can relieve the panic and/or anxiety of the object, especially, those suffering from claustrophobia, thereby reducing the object's movement due to anxiety and improving the efficiency and/or accuracy of the medical treatment and/or imaging.

FIG. 1 is a schematic diagram illustrating an exemplary display system according to some embodiments of the present disclosure. In some embodiments, the display system 100 may be applied to a medical imaging and/or treatment system, such as a positron emission tomography (PET) system, a single-photon emission computed tomography (SPECT) system, a magnetic resonance (MR) system, a computed tomography (CT) system, a radiotherapy system, or the like, or a combination thereof. In some embodiments, the display system 100 may be used in advertisement, traffic, sports, exhibition, performance and venue, smart home, car, interior decoration, etc. In some embodiments, the display system 100 may include modules and/or components for performing imaging and/or related analysis.

Merely by way of example, as illustrated in FIG. 1, the display system 100 may include one or more image acquisition devices 110, a control device 120, a storage device 130, one or more terminals 140, and a network 150. The components in the display system 100 may be connected in one or more of various ways. Merely by way of example, the one or more image acquisition devices 110 may be connected to the control device 120 through the network 150. As another example, the one or more image acquisition devices 110 may be connected to the control device 120 directly. As a further example, the terminal(s) 140 may be connected to another component of the display system 100 (e.g., the control device 120) via the network 150. As still a further example, the terminal(s) 140 may be connected to the control device 120 directly as illustrated by the dotted arrow in FIG. 1. As still a further example, the storage device 130 may be connected to another component of the display system 100 (e.g., the control device 120) directly as illustrated in FIG. 1, or through the network 150.

The one or more image acquisition devices 110 may be configured to acquire image data relating to at least one part of at least one of the one or more terminals 140 and/or image data relating to an object. For example, the one or more image acquisition devices 110 may include an optical imaging device and a radiation imaging device.

The optical imaging device may be configured to acquire the image data relating to at least one part of at least one of the one or more terminals 140, In some embodiments, the optical imaging device may include a camera, such as a wide-angle camera, a color camera, a digital video camera, a camcorder, a PC camera, a webcam, an infrared (IR) video camera, a low-light video camera, a thermal video camera, a CCTV camera, a pan, a tilt, a zoom (PTZ) camera, or the like, or a combination thereof. In some embodiments, the optical imaging device may include one or more image sensors, such as a charge coupled device (CCD), a complementary metal oxide semiconductor (CMOS), etc.

The radiation imaging device may be configured to acquire image data relating to an object. The image data relating to at least one part of an object may include a radiation image (e.g., an image slice), projection data, or a combination thereof. The object may be biological or non-biological. For example, the object may include a patient, a man-made object, etc. As another example, the object may include a specific portion, organ, and/or tissue of the patient. For example, the object may include the head, the neck, the thorax, the heart, the stomach, a blood vessel, soft tissue, a tumor, nodules, or the like, or any combination thereof. In some embodiments, the radiation imaging device may include a positron emission tomography (PET) device, a single-photon emission computed tomography (SPECT) device, a magnetic resonance imaging (MRI) device (also referred to as an MR device, an MR scanner), a computed tomography (CT) device, or the like, or any combination thereof. More descriptions for the one or more image acquisition devices 110 may be found in elsewhere in the present disclosure (e.g., FIGS. 2-5 and the descriptions thereof).

The control device 120 may process data and/or information obtained from the one or more image acquisition devices 110, the terminals) 140, and/or the storage device 130. For example, when the terminal 140 displays a content including a background portion and a target portion on its display panel, the control device 120 may obtain an image of the display panel of the terminal 140 from the one or more image acquisition devices 110. The display panel may include a frame area and a display area. The image of the display panel of the terminal 140 may include a representation of at least one portion of the frame area and at least one portion of the display area. The control device 120 may adjust the background portion of the content displayed on the display area based on the image of the display panel of the terminal 140. Specifically, the control device 120 may determine a reference value of an image parameter of the frame area and a value of the image parameter of the background portion represented in the image of the display panel. The control device 120 may determine a difference between the value of the image parameter of the background portion and the reference value of the image parameter of the frame area. The control device 120 may adjust one or more display parameters of the background portion to reduce the difference between the value of the image parameter of the background portion and the reference value of the image parameter of the frame area.

In some embodiments, the control device 120 may be a computer, a user console, a single server or a server group, etc. The server group may be centralized or distributed. In some embodiments, the control device 120 may be local or remote. For example, the control device 120 may access information and/or data stored in the one or more image acquisition devices 110, the terminal(s) 140, and/or the storage device 130 via the network 150. As another example, the control device 120 may be directly connected to the one or more image acquisition devices 110, the terminal(s) 140, and/or the storage device 130 to access stored information and/or data. In some embodiments, the control device 120 may be implemented on a cloud platform, Merely by way of example, the cloud platform may include a private cloud, a public cloud, a hybrid cloud, a community cloud, a distributed cloud, an inter-cloud, a multi-cloud, or the like, or any combination thereof. In some embodiments, the control device 120 may be integrated into one of the terminal(s) 140 and/or one of the image acquisition devices 110 (e.g., the optical imaging device).

The storage device 130 may store data, instructions, and/or any other information. In some embodiments, the storage device 130 may store data obtained from the terminal(s) 140 and/or the control device 120. The data may include image data acquired by the control device 120, algorithms and/or models for processing the image data, etc. For example, the storage device 130 may store image data acquired by the one or more image acquisition devices 110. As another example, the storage device 130 may store one or more algorithms for processing the image data. In some embodiments, the storage device 130 may store data and/or instructions that the control device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the display system 100 (e.g., the control device 120, the terminal(s) 140, etc.), One or more components in the display system 100 may access the data or instructions stored in the storage device 130 via the network 150. In some embodiments, the storage device 130 may be directly connected to or communicate with one or more other components in the display system 100 (e.g., the control device 120, the terminal(s) 140, etc.), In some embodiments, the storage device 130 may be part of the control device 120.

The terminal(s) 140 may include a device that be capable of display. For example, the terminal(s) 140 may include a display device. As another example, the terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a control device of an intelligent electrical apparatus, a smart monitoring device, a smart television, a smart video camera, an interphone, or the like, or any combination thereof. In some embodiments, the wearable device may include eyeglasses, a helmet, a watch, clothing, a backpack, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the control device 120.

The network 150 may include any suitable network that can facilitate the exchange of information and/or data for the display system 100. In some embodiments, one or more components of the one or more image acquisition devices 110 (e.g., an MRI device, a PET device, etc.), the terminal(s) 140, the control device 120, the storage device 130, etc., may communicate information and/or data with one or more other components of the display system 100 via the network 150. For example, the control device 120 may obtain data from the one or more image acquisition devices 110 via the network 150. As another example, the control device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the display system 100 may be connected to the network 150 to exchange data and/or information.

It should be noted that the above description of the display system 100 is merely provided for the purposes of illustration, and not intended to limit the scope of the present disclosure. For persons having ordinary skills in the art, multiple variations and modifications may be made under the teachings of the present disclosure. For example, the assembly and/or function of the display system 100 may be varied or changed according to specific implementation scenarios.

Figure 2:
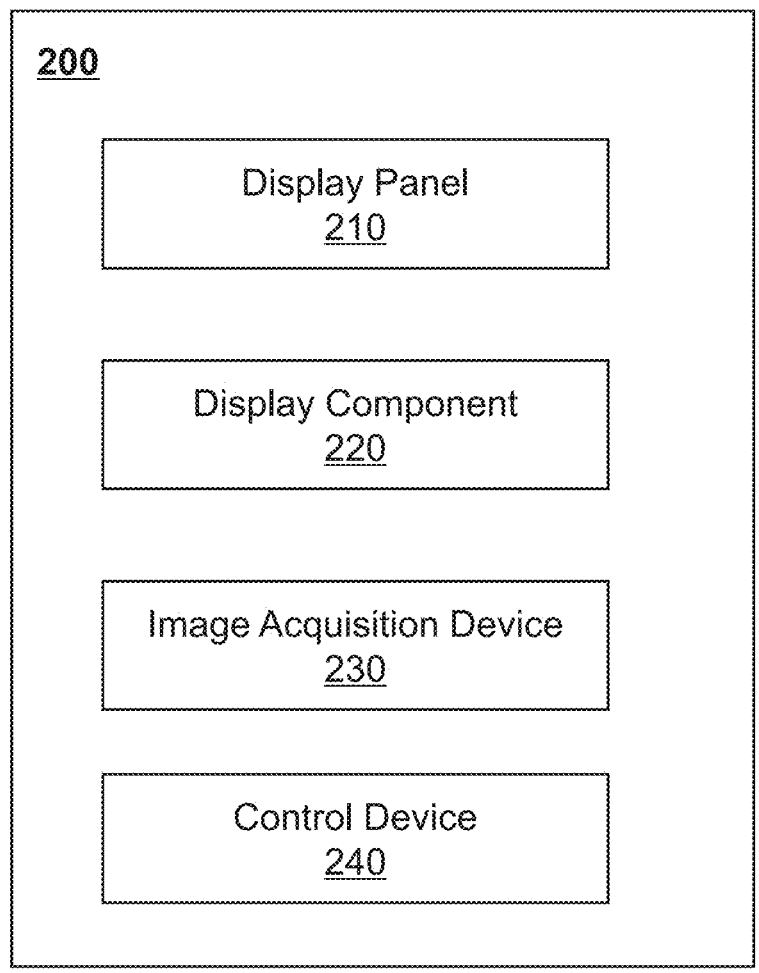
FIG. 2 is a block diagram illustrating an exemplary display apparatus according to some embodiments of the present disclosure.

FIG. 2 is a block diagram illustrating an exemplary display apparatus according to some embodiments of the present disclosure.

As illustrated in FIG. 2, a display apparatus 200 may include a display panel 210, a display component 220, an image acquisition device 230, and a control device 240.

Figure 6A:
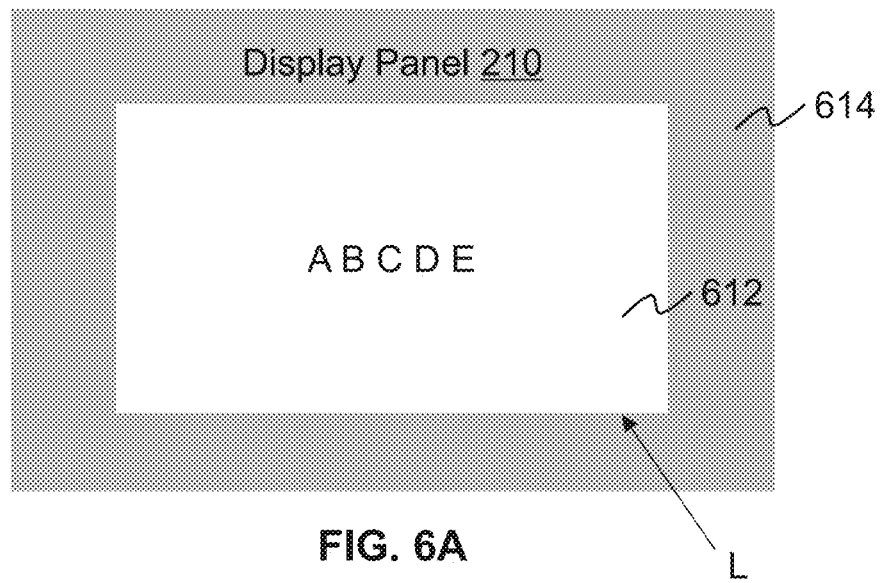
FIG. 6A is a schematic diagram of a display panel before adjusting one or more display parameters of a background portion of a content according to some embodiments of the present disclosure.

The display panel 210 may be configured to present a content (e.g., an image, a video, etc.). The display panel 210 may include a display area and a frame area (e.g., a display area 612 and a frame area 614 as shown in FIG. 6A). As used herein, a display area refers to an area where a content to be displayed can be presented on the display panel 210. In other words, the content to be displayed may be projected on the display area for display. A frame area refers to an area from the display area to an exterior periphery of the display panel

210. The frame area may also be referred to as a non-display area. The content to be display may be not projected on the non-display area. In some embodiments, the frame area may provide a support or protect for the display area.

In some embodiments, the display area may be made of a transparent material or a semi-transparent material, i.e., the display area may be a transparent area or a semi-transparent area. Exemplary transparent materials may include glass, polypropylene (PP), polycarbonate (PC), polystyrene (PS), polymethyl methacrylate (PMMA), etc. Exemplary semi-transparent materials may include low density polyethylene (LDPE), metals (e.g. Ag, Al, Mg, etc.), etc.

In some embodiments, the material of the frame area may include glass, polypropylene (PP), polycarbonate (PC), polystyrene (PS), polymethyl methacrylate (PMMA), low density polyethylene (LDPE), metals (e.g. Ag, Al, Mg, etc.), alloy (e.g., aluminum-magnesium alloy, titanium alloy), aluminum composite materials, or the like, or any combination thereof. In some embodiments, the frame area may be a transparent area, a semi-transparent area, or a non-transparent area.

In some embodiments, the material of the display area and the material of the frame area may be the same or different. For example, the display area and the frame area may be made of the same transparent material. In such cases, both the display area and the frame area may be a transparent area. As another example, the display area and the frame area may be made of a same transparent material and the frame area may be covered with a semi-transparent thin film. In such cases, the display area may be a transparent area while the frame area may be a semi-transparent area. As still an example, the material of the display area may be a transparent material and the material of the frame area may be a non-transparent material. In such cases, the display area may be a transparent area, and the frame area may be a non-transparent area.

In some embodiments, the display panel 210 may be flat or curved. For example, for a medical device including a gantry with a bore, the display panel 210 may be a portion or all of an inner surface of the gantry, and the inner surface of the gantry may be curved, i.e., the display panel 210 may be curved. As another example, the display panel 210 may be a portion or all of an outer surface of an exterior wall of a building, and the outer surface of the exterior wall of the building may be flat, i.e., the display panel 210 may be flat.

The display component 220 may be configured to present or project a content on the display area. In some embodiments, the content presented or projected on the display area of the display panel 210 may include a target portion and a background portion. The target portion and background portion presented or projected by the display component 220 may be displayed to a user through the display area. As used herein, the target portion of the content displayed by the display component 220 on the display area of the display panel 210 may include information that needs to be delivered to a user. The background portion of the content displayed by the display component 220 on the display area of the display panel 210 may be a portion other than the target portion of the content. The background portion of the content displayed by the display component 220 on the display area of the display panel 210 may not include information that needs to be delivered to a user. For example, as shown in FIG. 6A, for a rectangular display area 612, the target portion of the content are letters "A, B, C, D, E", the background portion of the content may be the white portion (i.e., the blank area) of the display area 612. In some embodiments, the target portion may include a letter, a number, a symbol, a pattern (e.g., a geometric pattern, an animal pattern, a constellation pattern), or the like, or any combination.

In some embodiments, the display component 220 may include a light emitting element, such as a thin film transistor (TFT) liquid crystal, an organic light-emitting diode (OLED), a LED dot matrix, a micro light-emitting diode (micro LED), a plasma light emitting element, a projector, or the like, or any combination thereof. In some embodiments, the display panel 210 and the display component 220 may be integrated into one component. For example, the display component 220 may include a TFT-LCD display, an OLED display, a LED dot matrix display, a micro LED display, a plasma display panel, or the like, or any combination thereof.

In some embodiments, the display component 220 may be located at a first side of the display panel 210. In some embodiments, the display component 220 may be spaced apart from the display panel 210 at the first side. In some embodiments, the display component 220 may be physically connected with the display panel 210. For example, when the display component 220 includes a LED dot matrix display, the LED dot matrix display may be installed on the first side of the display panel 210 by, for example, an adhesive. In such cases, a size of the display component 220 may be the same as a size of the display area of the display panel 210. See, e.g., an exemplary structure of the display apparatus 300 shown in FIG. 3. As another example, when the display component 220 includes a projector, the projector may be spaced apart from the display panel 210. The projector may project the content on the display area of the display panel 210. In such cases, a size of the projected area may be the same as the size of the display area. See, e.g., exemplary structures of the display apparatus 400 and/or 500 as shown in FIG. 4 or FIG. 5.

In some embodiments, the display component 220 may emit light beams and the light beams may be projected on the display area of the display panel 210 to form the content to be displayed. In some embodiments, the display component 220 may include a plurality of display units each of which can operate or be controlled independently to display the content. Each display unit may be controlled to emit a light beam with characteristics such as color, brightness, etc. The characteristics of the light beams corresponding to the background portion of the content may be different from the characteristics of the light beams corresponding to the target portion of the content. In some embodiments, the characteristics of the light beams corresponding to the background portion of the content may be the substantially same (e.g., having the same color and/or same brightness) or consistent. In some embodiments, the display units for emitting light beams corresponding to the background portion of the content may be turned off. For example, when the display component 220 includes nine display units arranged as a matrix 3×3, the display units in the middle column of the matrix may be turned on to emit light beams, and the display units other than the middle column may be turned off and do not emit light beams, so that the target portion of the content may be displayed as the number "1", and the display units turned off may correspond to the background portion.

The image acquisition device 230 may be configured to acquire an image of the display panel 210. The image may include a representation of at least a portion of the frame area and at least a portion of the display area of the display panel 210. In some embodiments, when the content is displayed in the display area of the display panel 210, the image acquisition device 230 may acquire the image including the representation of the at least a portion of the frame area and the background portion of the content displayed in the display area of the display panel 210.

In some embodiments, the image acquisition device 230 may include a wide-angle camera, a color camera, a digital video camera, a camcorder, a PC camera, a webcam, an infrared (IR) video camera, a low-light video camera, a thermal video camera, a CCTV camera, a pan, a tilt, a zoom (PTZ) camera, or the like, or a combination thereof.

In some embodiments, the image acquisition device 230 may be located at the first side or a second side of the display panel 210. That is, the display component 220 and the image acquisition device 230 may be at a same side or different sides of the display panel 210. A field of view (FOV) of the image acquisition device 230 may cover the at least one portion of the frame area and the at least one portion of the display area. For example, when the display component 220 includes a projector, the projector and the image acquisition device 230 may be located at the same side of the display panel 210. In some embodiments, the image acquisition device 230 may be arranged from the display panel 210 within a distance (e.g., as shown in FIG. 3 or FIG. 4).

Figure 3:
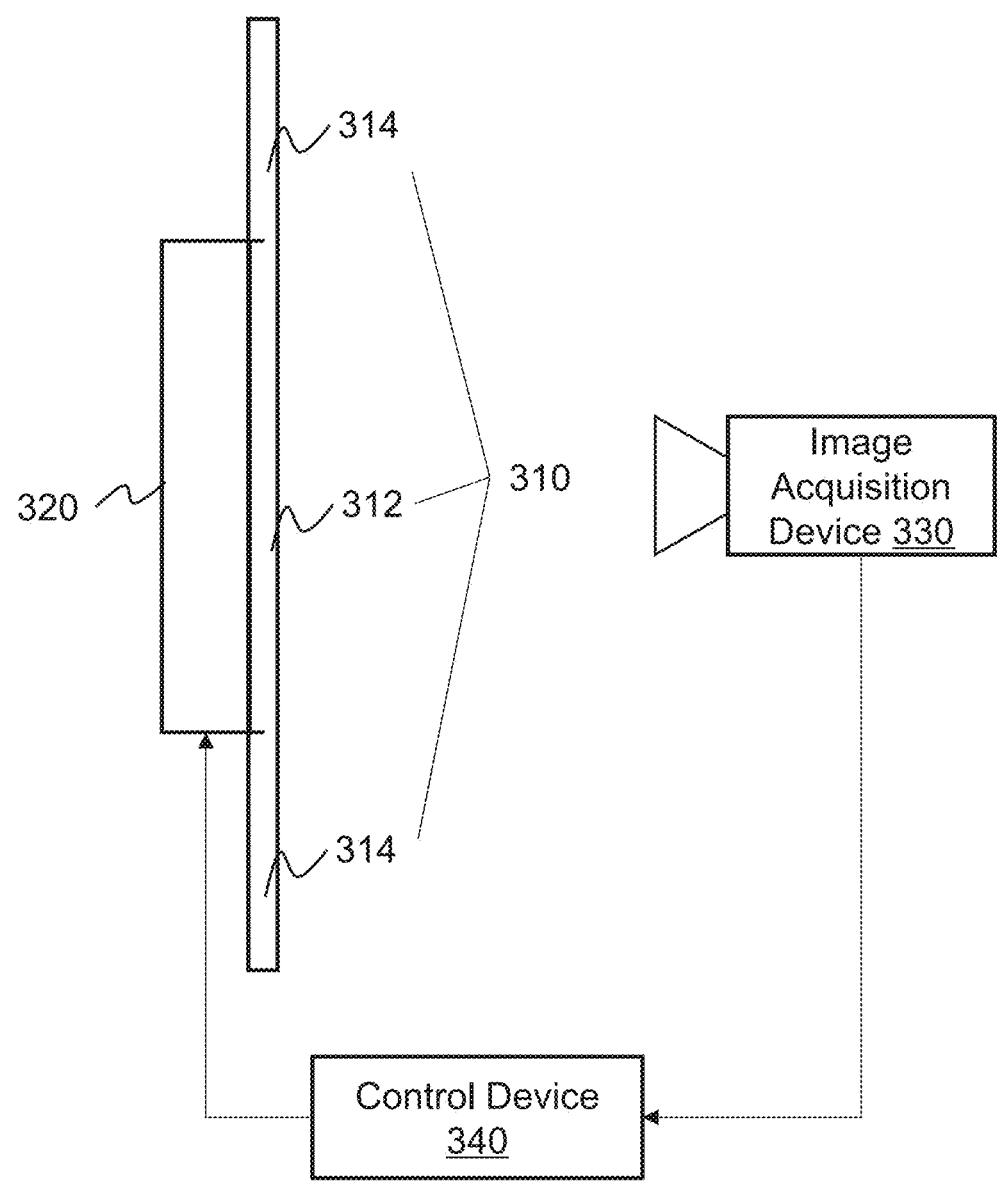
FIG. 3 is a schematic diagram illustrating an exemplary display apparatus according to some embodiments of the present disclosure.
Figure 4:
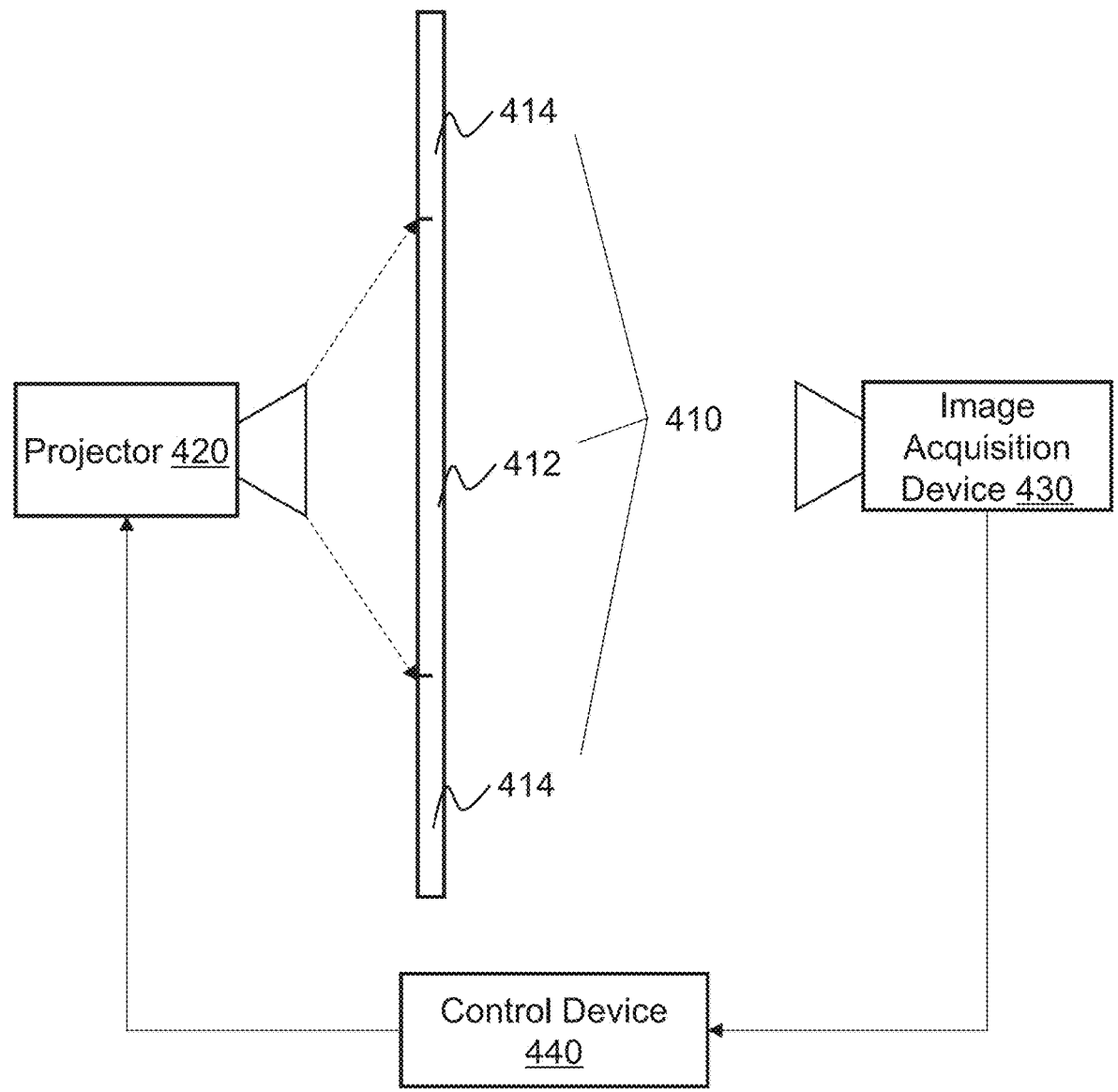
FIG. 4 is a schematic diagram illustrating an exemplary display apparatus according to some embodiments of the present disclosure.
Figure 5:
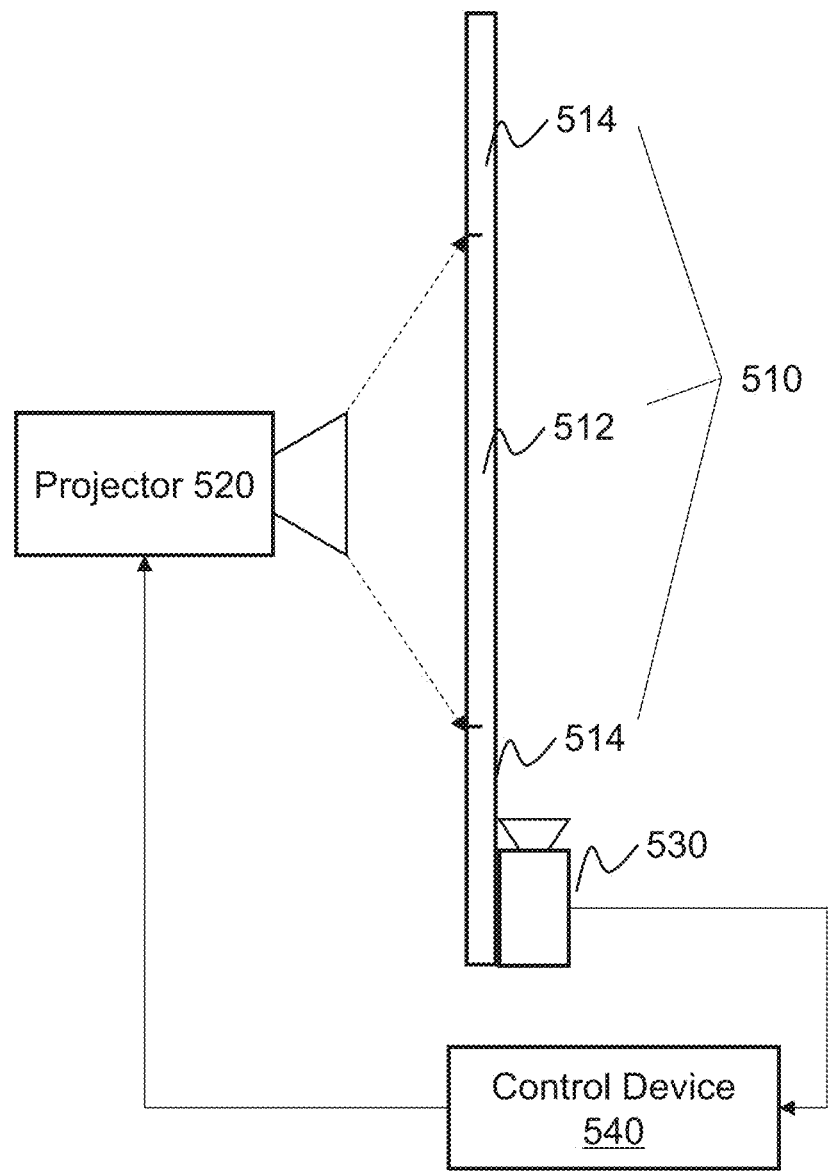
FIG. 5 is a schematic diagram illustrating an exemplary display apparatus according to some embodiments of the present disclosure.

In some embodiments, when the image acquisition device 230 is spaced apart from the display panel 210 (as shown in FIG. 3 or FIG. 4), the image acquisition device 230 may include a traditional camera or a wide-angle camera. In some embodiments, when the image acquisition device 230 is a wide-angle camera, the wide-angle camera may be installed on a position (e.g., any portion of the frame area) of the display panel 210 as shown in FIG. 5, thereby reducing a volume of the display apparatus 200 and facilitating installation. For example, the wide-angle camera may be installed obliquely at a position of the frame area of the display panel 210 to enable a FOV of the wide-angle camera covers the at least one portion of the frame area and the at least one portion of the display area of the display panel 210.

The control device 240 may be configured to control the operation of components of the display apparatus 200. For example, the control device 240 may control the turn on or off of the image acquisition device 230 and/or the display component 220 according to an input of a user or according to a default setting of the display apparatus 200. As another example, the control device 240 may control the display component 220 to display a content on the display panel 210. As still another example, the control device 240 may control the display component 220 to adjust the background portion of the content displayed on the display area according to the image of the display panel 210 acquired by the image acquisition device 230 according to process 800 as illustrated in FIG. 8. In some embodiments, the control device 240 may include one or more hardware processors, such as a microcontroller, a microprocessor, a reduced instruction set computer (RISC), an application-specific integrated circuit (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof. The control device 240 may be connected to the display component 220 and/or the image acquisition device 230 via a wired connection, a wireless connection, or a combination thereof. The wired connection may include, for example, an electrical cable, an optical cable, a telephone wire, or the like, or any combination thereof. The wireless connection may include a Bluetooth™ network, a local area network (LAN), a wide area network (WAN)), a near field communication (NFC) network, a ZigBee™ network, or the Ike or any combination thereof.

In some embodiments, the control device 240 may determine a reference value of an image parameter of the frame area and a value of the image parameter of the background portion represented in the image of the display panel 210. The control device 240 may control the display component 220 to adjust one or more display parameters of the background portion according to the value of the image parameter of the background portion and the reference value of the image parameter of the frame area. In some embodiments, the image parameter may include a color parameter, a brightness parameter, or the like, or a combination thereof. Exemplary values of the color parameter and/or the brightness parameter of the image may be denoted by RGB (Red, Green, Blue) values, HSV (Hue, Saturation, Value) values, HSB (Hue, Saturation, Brightness) values, CMYK (Cyan, Magenta, Yellow, Black) values, etc. The image parameter may be denoted by pixel values in the image. For example, the value of the image parameter may be denoted by an average of pixels values in the image, or a maximum pixel value, or a minimum pixel value, etc. In some embodiments, for the background portion of the content, pixel values representing the background portion of the content in the image may be substantially the same. As used herein, the one or more display parameters of the background portion may be configured to adjust one or more characteristics of light beams generated by one or more display units of the display component 220 corresponding to the background portion of the content. In some embodiments, the one or more display parameters of the background portion may also be referred to as display parameter(s) of the corresponding display unit(s). For example, the control device 240 may transmit a control signal to the one or more display units corresponding to the background portion of the content to adjust the one or more display parameters of the corresponding display unit(s) based on a difference between the value of the image parameter of the background portion and the reference value of the image parameter of the frame area. As a further example, the control device 240 may transmit the control signal to the one or more display units corresponding to the background portion of the content to adjust characteristics of light beams emitted by the corresponding display unit(s) to reduce the difference between the value of the image parameter (e.g., an average pixel value) of the background portion and the reference value (e.g., an average pixel value) of the image parameter of the frame area.

In some embodiments, after adjusting the one or more display parameters of the background portion, the difference between the value of the image parameter of the background portion and the reference value of the image parameter of the frame area may be smaller than a threshold. Preferably, after adjusting the one or more display parameters of the background portion, the value of the image parameter of the background portion may be the same as the reference value of the image parameter of the frame area. In such cases, the area of the display panel 210 corresponding to the background portion of the content and the frame area of the display panel 210 may be visually the same or consistent (or substantially the same), that is, the background portion of the content may be visually hidden (e.g., as shown in FIG. 3B), thus achieving borderless display.

In some embodiments, the control device 240 may further determine a value of the image parameter of the target portion represented in the image. The control device 240 may adjust one or more display parameters of the target portion based on the value of the image parameter of the target portion and the reference value of the image parameter of the frame area. For example, a difference between the value of the image parameter of the target portion and the reference value of the image parameter of the frame area may be adjusted to be greater or equal to a threshold. For instance, at the night, the one or more display parameters of the target portion may be adjusted to make the target portion brighter, so that the user can see the target portion clearly.

In some embodiments, the image acquisition device 230 may acquire images of the display panel 210 continuously or periodically, for example, per 100 ms and the control device 240 may adjust the one or more the display parameters of the target portion in real time according to each of the images. For example, as the ambient light changes, the frame area and/or the area corresponding to the target portion may reflect different colors and/or brightness, the control device 240 may adjust the one or more display parameters of the target portion in real time according to the ambient light. In such cases, the background portion of the content may be visually hidden from time to time regardless of the ambient light, thus achieving borderless display. In some embodiments, the frame rate of the display component 220 may be the same as or less than the frame rate of the image acquisition device 230, such that each frame of the display component 220 may be adjusted based on an image acquired by the image acquisition device 230 at a same time.

It should be noted that the above description of the display apparatus 200 is merely provided for the purposes of illustration, and not intended to limit the scope of the present disclosure. For persons having ordinary skills in the art, multiple variations and modifications may be made under the teachings of the present disclosure. For example, the image acquisition device 230 may include two image acquisition units which may acquire an image of the frame area of the display area and an image of the background portion of the content displayed on the display area, respectively. In some embodiments, the control device 240 may be integrated into the image acquisition device 230 or may be provided as a separate processor.

FIG. 3 is a schematic diagram illustrating an exemplary display apparatus according to some embodiments of the present disclosure. The display apparatus 300 may be the same as or similar to the display apparatus 200 as described in FIG. 2. For example, the display apparatus 300 may include a display panel 310, a display component 320, an image acquisition device 330, and a control device 340. The display panel 310 may include a display area 312 and a frame area 314. More descriptions for components of the display apparatus 300 may be found elsewhere in the present disclosure (e.g., FIG. 2 and the descriptions thereof).

The display component 320 may be located at a first side of the display panel 310 and physically connected with the display panel 310, especially connected with the display area 312. For example, the display component 320 may be connected with the display panel 310 by, for example, an adhesive, bonding, etc. In some embodiments, a size of the display component 320 may be the same as a size of the display area 312 of the display panel 310.

In some embodiments, the display component 220 includes a LED dot matrix, a TFT-LCD, an OLED, a micro LED, etc.

The image acquisition device 330 may be arranged at a second side of the display panel 310 that is opposite to the first side. For example, the image acquisition device 330 may be arranged at the second side of the display panel 310 along a horizontal central line of the display panel 310. The FOV of the image acquisition device 330 may include at least a portion of the display area 312 and at least a portion of the frame area 314.

FIG. 4 is a schematic diagram illustrating an exemplary display apparatus according to some embodiments of the present disclosure. The display apparatus 400 may be the same as or similar to the display apparatus 200 as described in FIG. 2, For example, the display apparatus 400 may include a display panel 410, a projector 420, an image acquisition device 430, and a control device 440. The display panel 410 may include a display area 412 and a frame area 414. More descriptions for components of the display apparatus 400 may be found elsewhere in the present disclosure (e.g., FIG. 2 and the descriptions thereof).

The projector 420 may be located at a first side of the display panel 410 and be spaced apart from the display panel 410 within a distance. For example, the projector 420 may be arranged at the first side of the display panel 410 along a horizontal central line of the display panel 410. In some embodiments, a size of the projected area of the projector 420 may be the same as a size of the display area 412 of the display panel 410.

In some embodiments, the image acquisition device 430 may be arranged at the first side of the display panel 410 or a second side of the display panel 410 that is opposite to the first side. In other words, the projector 420 and the image acquisition device 430 may be arranged at the same side or different sides of the display panel 410. For example, the image acquisition device 430 may be arranged at the second side of the display panel 410 along a horizontal central line of the display panel 410. The FOV of the image acquisition device 430 may include at least a portion of the display area 412 and at least a portion of the frame area 414.

FIG. 5 is a schematic diagram illustrating an exemplary display apparatus according to some embodiments of the present disclosure. The display apparatus 500 may be the same as or similar to the display apparatus 200 as described in FIG. 2. For example, the display apparatus 500 may include a display panel 510, a projector 420, a wide-angle camera 530, and a control device 540. The display panel 510 may include a display area 512 and a frame area 514. More descriptions for components of the display apparatus 500 may be found elsewhere in the present disclosure (e.g., FIG. 2 and the descriptions thereof).

The projector 520 may be located at a first side of the display panel 510 and be spaced apart from the display panel 510 within a distance. For example, the projector 520 may be arranged at the first side of the display panel 510 along a horizontal central line of the display panel 510. In some embodiments, a size of the projected area of the projector 520 may be the same as a size of the display area 512 of the display panel 510.

The wide-angle camera 530 may be located at a second side of the display panel 510 that is opposite to the first side and physically connected with the display panel 510, especially connected with a position of the frame area 514. For example, the wide-angle camera 530 may be connected with the display panel 510 by, for example, an adhesive, bonding, etc. The FOV of the wide-angle camera 530 may include at least a portion of the display area 512 and at least a portion of the frame area 514.

Figure 6B:
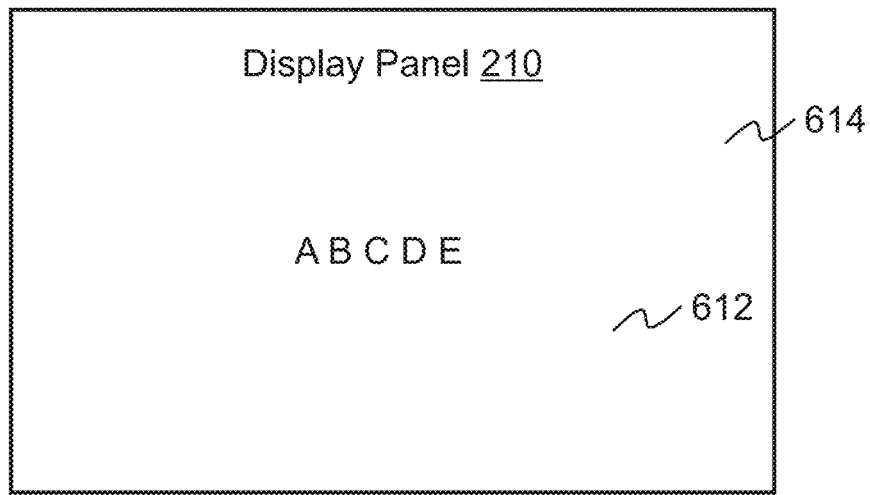
FIG. 6B is a schematic diagram of a display panel after adjusting one or more display parameters of a background portion of a content according to some embodiments of the present disclosure.

In some embodiments, the wide-angle camera 530 may be arranged at the bottom portion of the display panel 510. In some embodiments, the wide-angle camera 530 may be arranged at the top portion of the display panel 510, FIG. 6A is a schematic diagram of a display panel 210 before adjusting one or more display parameters of a background portion of a content according to some embodiments of the present disclosure. FIG. 6B is a schematic diagram of a display panel 210 after adjusting one or more display parameters of a background portion of a content according to some embodiments of the present disclosure. As illustrated in FIG. 6A, the display panel 210 may include a display area 612 and a frame area 614. The display area 612 represents a content including a target portion and a background portion. The target portion of the content are letters "A B C D E." The background portion of the content corresponds to the white portion in the display area 612 in FIG. 6A.

According to FIG. 6A, before adjusting the one or more display parameters of the background portion, the appearance of the background portion is different from that of the frame area 614 (e.g., different colors or different brightness), which causes a boundary L between the display area 612 and the frame area 614 visually. According to FIG. 68, after adjusting the one or more display parameters of the background portion as described in FIG. 2, the value of the image parameter of the background portion may be the same as (or substantially same as) the reference value of the image parameter of the frame area 612. The boundary L between the display area 612 and the frame area 614 may disappear visually. In such cases, the user may only visually see the target portion of the content on the display panel 210, which improves the user viewing experience.

Figure 7:
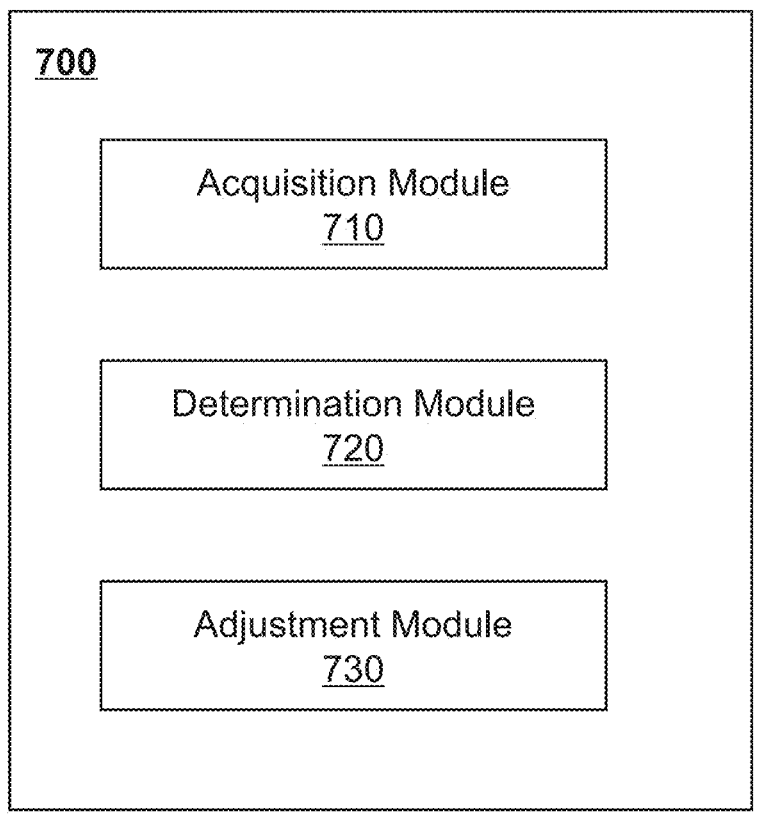
FIG. 7 is a block diagram illustrating an exemplary control device according to some embodiments of the present disclosure.

FIG. 7 is a block diagram illustrating an exemplary control device according to some embodiments of the present disclosure. The control device 700 may be exemplary control device 120 or 140 as described in connection with FIG. 1 or 2. As illustrated in FIG. 7, the control device 700 may include an acquisition module 710, a determination module 720, and an adjustment module 730. The modules may be hardware circuits of all or part of the control device 700. The modules may also be implemented as an application or set of instructions read and executed by the control device 700. Further, the modules may be any combination of the hardware circuits and the application/instructions. For example, the modules may be part of the control device 700 when the control device 700 is executing the application/set of instructions.

The acquisition module 710 may be configured to obtain an image of a display panel of a display apparatus. The display panel may include a frame area and a display area, A content (e.g., an image) including a target portion and a background portion may be displayed on the display area. The image of the display panel may include a representation of at least a portion of the frame area and at least a portion of the display area where the background portion of the content is displayed.

The determination module 720 may be configured to determine a reference value of an image parameter of the frame area and a value of the image parameter of the background portion represented in the image of the display panel. The determination module 720 may determine a difference between the value of the image parameter of the background portion and the reference value of the image parameter of the frame area.

The adjustment module 730 may be configured to adjust one or more display parameters of the background portion according to the value of the image parameter of the background portion and the reference value of the image parameter of the frame region. The one or more display parameters of the background portion may be configured to control characteristics of light beams generated by sub-units corresponding to the background portion of the content. For example, the control device 240 may transmit a control signal to the display units corresponding to the background portion of the content to adjust the one or more display parameters of the corresponding display unit(s) based on the difference between the value of the image parameter of the background portion and the reference value of the image parameter of the frame area. As a further example, the control device 240 may transmit the control signal to the one or more display units corresponding to the background portion of the content to adjust characteristics of light beams emitted by the corresponding display unit(s) to reduce the difference between the value of the image parameter (e.g., an average pixel value) of the background portion and the reference value (e.g., an average pixel value) of the image parameter of the frame area.

The modules in the control device 700 may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined into a single module, and any one of the modules may be divided into two or more units. For example, the acquisition module 710 may be divided into two units configured to obtain an image of the frame area of the display panel and obtain an image of the background portion of the content respectively. As another example, the control device 700 may further include a storage module configured to store data and/or information (e.g., the image of the display panel, values of the image parameter of the image of the display panel) associated with the display apparatus 200.

FIG. 8 is a flowchart illustrating an exemplary process for borderless display according to some embodiments of the present disclosure. In some embodiments, process 800 may be implemented as a set of instructions (e.g., an application) stored in a storage device. The control device 120 or 240 may execute the set of instructions, and when executing the instructions, the control device 120 or 240 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of the process 800 illustrated in FIG. 8 and described below is not intended to be limiting.

In 810, the control device 240 may obtain an image of a display panel of a display apparatus. The display apparatus may be described elsewhere in the represent disclosure (e.g., FIGS. 2-5 and the descriptions thereof). For example, the display panel may include a frame area and a display area as described in connection with the display panel 210 of the display apparatus 200 in FIG. 2. A content (e.g., an image) including a target portion and a background portion may be displayed on the display area. The image of the display panel may include a representation of at least a portion of the frame area and at least a portion of the display area where the background portion of the content is displayed.

In some embodiments, the image of the display panel may be obtained from an image acquisition device (e.g., the image acquisition device 230) or any other storage device. For example, the image acquisition device may transmit the acquired image to a storage device. The control device 240 may obtain the image from the storage device. As another example, the control device 240 may obtain the image from the image acquisition device directly.

In 820, the control device 240 may determine a reference value of an image parameter of the frame area represented in the image of the display panel. In some embodiments, the image parameter may include a color parameter, a brightness parameter, or the like, or a combination thereof. In some embodiments, the image parameter may be denoted by pixel values in the image. For example, if the image includes a gray-level image, the image parameter (e.g., the brightness) may be denoted by gray values of pixels in the image; if the image includes a color image, the image parameter may be denoted by color values (e.g., RGB values, HVS values) of pixels in the image. In some embodiments, the pixel values of the frame area represented in the image of the display panel may be substantially the same or consistent. The control device 240 may designate an average, a mid-value, a maximum value, a minimum value, etc., of the pixel values of the frame area represented in the image of the display panel as the reference value of the image parameter of the frame area represented in the image of the display panel.

In 830, the control device 240 may determine a value of the image parameter of the background portion represented in the image. In some embodiments, the pixel values of the background portion represented in the image of the display panel may be substantially the same or consistent. The control device 240 may designate an average, a mid-value, a maximum value, a minimum value, etc., of the pixel values of the background portion represented in the image of the display panel as the value of the image parameter of the background portion represented in the image of the display panel.

In 840, the control device 240 may adjust one or more display parameters of the background portion according to the value of the image parameter of the background portion and the reference value of the image parameter of the frame region. The one or more display parameters of the background portion may be configured to control characteristics of light beams generated by display units corresponding to the background portion of the content. In some embodiments, the control device 240 may adjust the one or more display parameters of the background portion based on a difference between the value of the image parameter of the background portion and the reference value of the image parameter of the frame area. For example, the control device 240 may transmit a control signal to the display units corresponding to the background portion of the content to adjust values of the one or more display parameters of the corresponding display unit(s) to be the same as the reference value of the image parameter of the frame area. As another example, the control device 240 may transmit a control signal to the display units corresponding to the background portion of the content to adjust characteristics of light beams emitted by the corresponding display unit(s) to reduce the difference between the value of the image parameter (e.g., an average pixel value) of the background portion and the reference value (e.g., an average pixel value) of the image parameter of the frame area.

In some embodiments, after adjusting the one or more display parameters of the background portion, a difference between the value of the image parameter of the background portion and the reference value of the image parameter of the frame area may be smaller than a threshold. Preferably, after adjusting the one or more display parameters of the background portion, the value of the image parameter of the background portion may be the same as the reference value of the image parameter of the frame area. In such cases, the area of the display panel 210 corresponding to the background portion of the content and the frame area of the display panel 210 may be visually the same (or substantially the same), that is, the background portion of the content may be visually hidden, thus achieving borderless display.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted, and/or one or more additional operations may be added. For example, operation 820 and operation 830 may be combined into a single operation. As another example, the control device 240 may further determine a value of the image parameter of the target portion represented in the image. The control device 240 may adjust one or more display parameters of the target potion based on the value of the image parameter of the target portion and the reference value of the image parameter of the frame area.

Figure 9A:
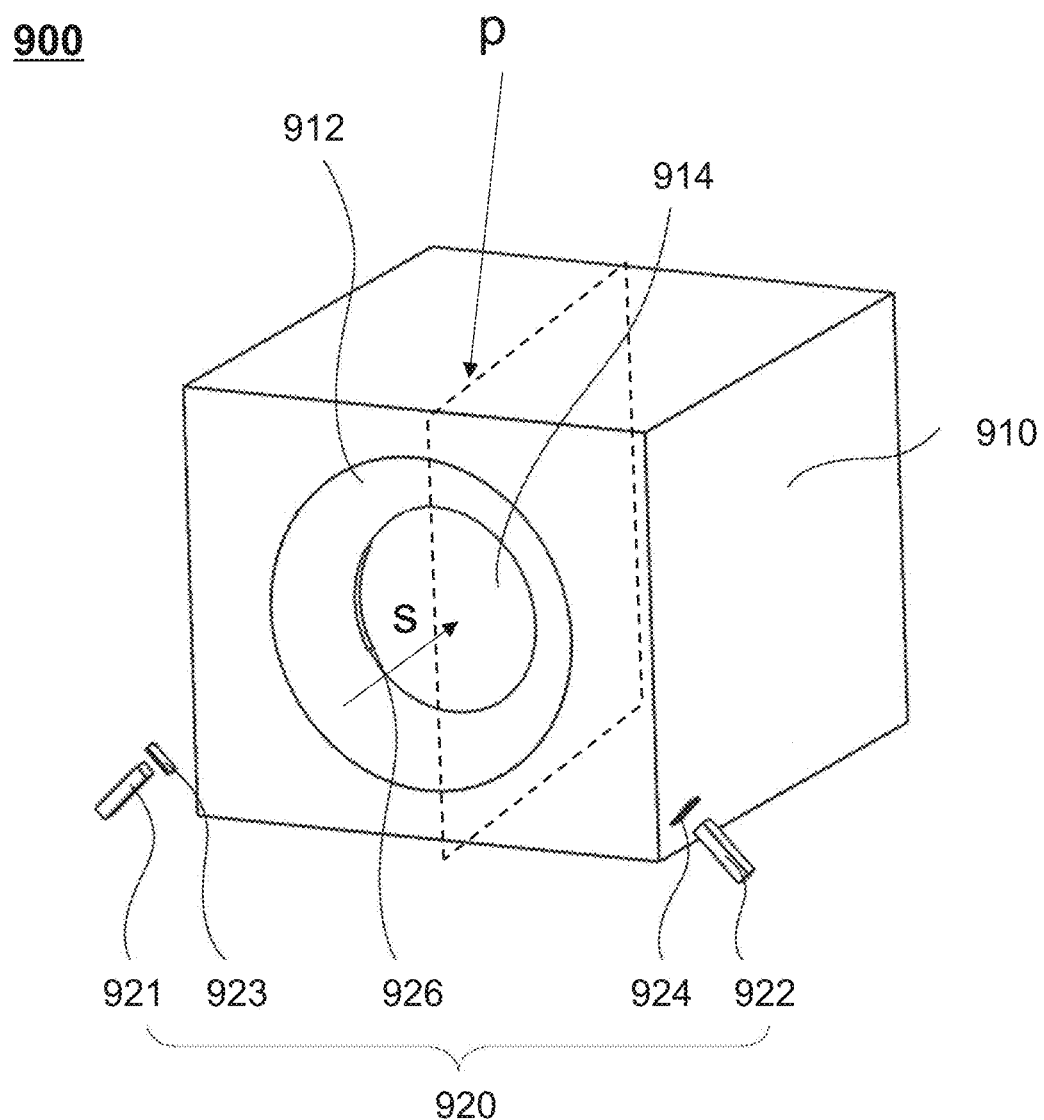
FIG. 9A is a schematic diagram illustrating an exemplary gantry of a medical device according to some embodiments of the present disclosure.
Figure 9B:
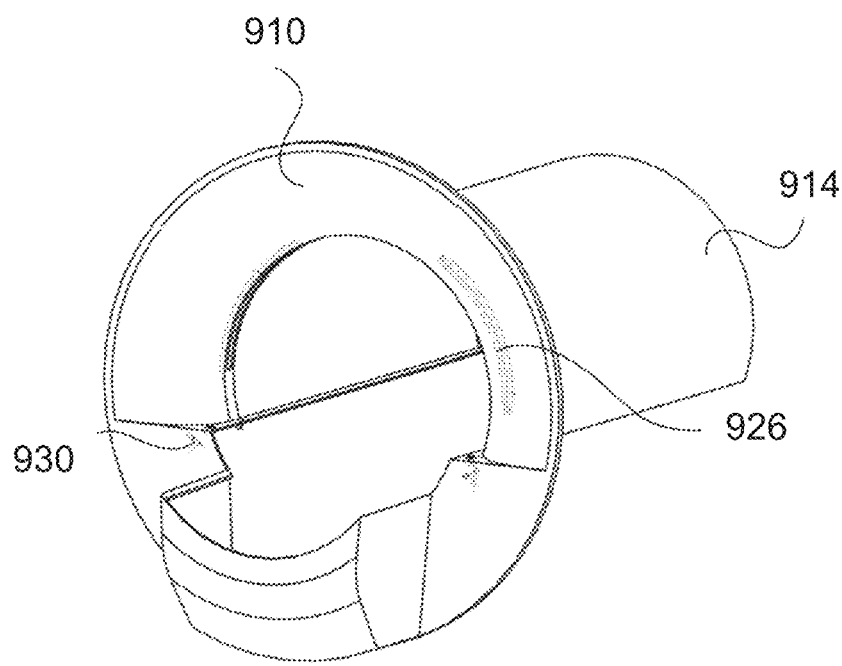
FIG. 9B is a perspective view illustrating the gantry of the medical device as shown in FIG. 9A viewed from a direction according to some embodiments of the present disclosure.
Figure 9C:
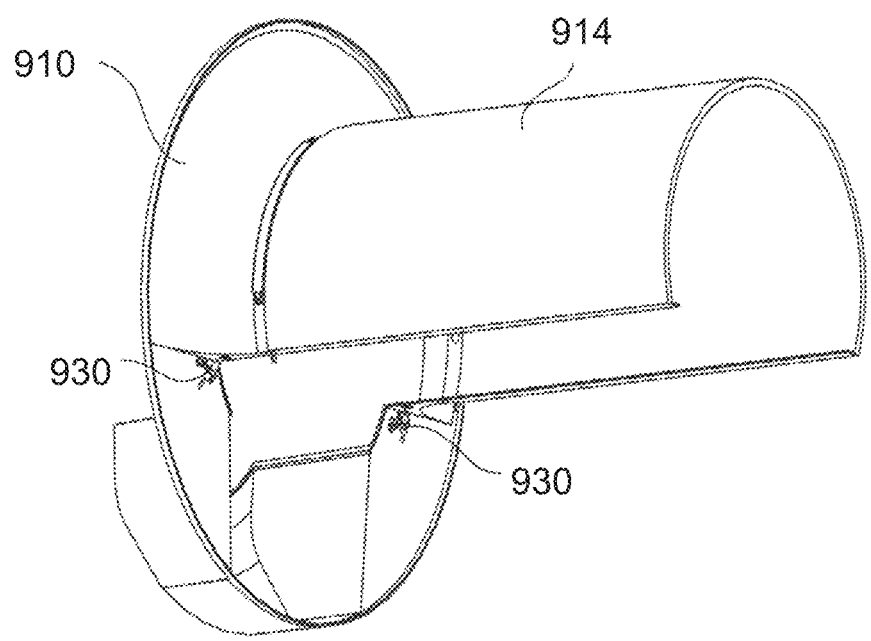
FIG. 9C is a perspective view illustrating the gantry of the medical device as shown in FIG. 9A viewed from another direction according to some embodiments of the present disclosure.

FIG. 9A is a schematic diagram illustrating an exemplary gantry of a medical device according to some embodiments of the present disclosure. FIGS. 9B and 9C are perspective views illustrating the gantry of the medical device as shown in FIG. 9A viewed from different directions according to some embodiments of the present disclosure.

As illustrated in FIG. 9A, a medical device 900 may include a gantry 910 and a lighting device 920.

The gantry 910 may include a bore 914 configured to accommodate an object (e.g., a patient). A length of the bore 914 in an axial direction denoted by arrow S in FIG. 9A of the gantry 910 may be in a length range (e.g., from 1.0 m to 2.0 m). For example, the object may be on a couch and be moved with a couch along the axial direction of the gantry 910 to the bore 914 for medical treatment and/or imaging. In some embodiments, the axial direction of the gantry 910 may also be referred to as an axial direction of the bore 914, or a sagittal axial of the gantry 910 or the bore 914. The gantry 910 may accommodate and/or support components of the medical device 900 that are used for medical treatment and/or imaging, such as coils, a radiation source, a detector, etc. For example, the radiation source (e.g., a tube) may generate radiation rays, and the detector may detect the radiation rays penetrated through at least part of the object for imaging. In some embodiments, an outer surface of the gantry 910 may be provided with a control panel for facilitating a communication between the medical device and an operator (e.g., a doctor). For example, the control panel may be configured with one or more keys or buttons for controlling the medical device 900 by the operator.

In some embodiments, the medical device 900 may include a computed tomography (CT) device (e.g., a cone beam computed tomography (CBCT) device, a fan-beam computed tomography (FBCT) device), a magnetic resonance imaging (MRI) device, a single photon emission computed tomography (SPECT) device, a positron emission tomography (PET) device, a radiotherapy device, etc., or any other medical device that has a bore.

The lighting device 920 may include one or more light sources and one or more display apparatuses. For illustration purposes, the lighting device 920 may include two light sources 921 and 922, and two display apparatuses 923 and 924 as shown in FIG. 9A.

In some embodiments, the light sources 921 and 922 may be configured to provide lighting for the bore 914. In some embodiments, at least one of the light sources 921 and 922 may be arranged at an end of the sagittal axial of the gantry 910. For example, the light source 922 may be obliquely disposed at an end of the gantry 910 corresponding to an entrance of the bore 914, as illustrated in FIG. 9A. In such cases, a light beam generated by the light source 922 may be projected into the bore 914, which may avoid mutual interference between the light source 922 and the radiation source in the medical device 900, thereby ensuring the accuracy and reliability of the medical device 900. As another example, the two light sources 921 and 922 may be arranged at two ends of the sagittal axial of the gantry 910 to ensure that the bore 914 is bright and avoid blind spots. In some embodiments, distances from the two light sources 921 and 922 to the sagittal axial of the gantry 910 may be the same or different. Merely by way of example, the two light sources 921 and 922 may be symmetrically arranged at two sides of a sagittal plane denoted by dotted box P in FIG. 9A of the gantry 910.

In some embodiments, at least one of the light sources 921 and 922 may include a laser light, a LED light, or the like, or any combination thereof. For example, due to a low attenuation of light intensity of the laser light, the light source 922 may be the laser light to ensure the brightness intensity of the light source.

In some embodiments, characteristics (e.g., the brightness, color, etc.) of the light beams generated by the light source 921 and the light source 922 may be the same or different. For example, the light beams of the light source 921 and the light source 922 may have the same or different colors, same or different brightness intensities, etc., to adapt to different needs (e.g., to achieve staggered display). As another example, a brightness intensity of the light source 922 may be kept constant and a brightness intensity of the light source 921 may change at a certain frequency. As still an example, a frequency of changing the brightness intensity or color of the light source 921 may be different from that of the light source 922. In some embodiments, the color of the light beam may include red, green, blue, yellow; etc. It should be noted that when the light beams generated by the light source 921 and the light source 922 are the same or different, the color of the light source 921 and the light source 922 may be the same or different.

In some embodiments, the display apparatuses 923 and 924 may be configured to display a content on a display panel. In some embodiments, the display panel may be arranged on or physically connected with the inner surface of the gantry 910. In some embodiments, the display panel may include the inner surface of the gantry 910. The display apparatuses 923 and 924 may be configured to display the content on the inner surface of the gantry 910. In some embodiments, the content may include a pattern (e.g., a geometric pattern, an animal pattern, a plant pattern, a constellation pattern, etc.), a video, an image, a letter, a number, a symbol, or the like, or any combination thereof. The content may be projected on the inner surface of the gantry 910 that the object (e.g., a child, a patient) located in the bore 914 can see, which may reduce claustrophobia of the object, and make the object better cooperate with the imaging and/or treatment, thereby improving the efficiency of imaging and/or treatment.

In some embodiments, the inner surface of the gantry 910 may be served as the display panel that includes a frame area and a display area. Each of the display apparatuses 923 and 924 may include a display component configured to display the content including a target portion and a background portion on the display area.

In some embodiments, at least one of the display apparatus 923 and the display apparatus 924 may further include an image acquisition device configured to acquire an image of the inner surface of the gantry 910. The image may include at least a portion of the frame area and at least a portion of the display area. In some embodiments, at least one of the display apparatus 923 and the display apparatus 924 may further include a control device configured to control the display component to adjust the background portion of the content displayed on the display area according to the image of the inner surface of the gantry 910, More descriptions about the display apparatus including a display panel, a display component, an image acquisition device, and/or a control device may be found elsewhere in the present disclosure (e.g., FIG. 2 and the descriptions thereof).

In some embodiments, the display component may include diffraction components. The number/count of the diffraction components may be the same as a number/count of the light sources. Each of the diffraction components may correspond to one light source. As used herein, a diffraction component corresponding to a fight source may refer that light beams of the light source may traverse the corresponding diffraction component. For example, a diffraction component and the corresponding light source may be located at an end of the sagittal axial of the gantry 910, such as an end where the entrance of the bore 914 is located. As another example, when the two light sources 921 and 922 are arranged at two ends of the sagittal axial of the gantry 910, the corresponding two diffraction components may also be arranged at the two ends of the sagittal axial of the gantry 910.

The diffraction component may be configured to generate the content based on the light beams generated by the corresponding light source and display the content on the inner surface of the gantry 910. For example, the diffraction component may be located at an irradiation path of the light source so that the light beams emitted by the light source can be projected into the bore 914 through the diffraction component. In some embodiments, the diffraction component may include a grating element, a film, etc.

The diffraction component may include a pattern configured to provide the content for display. The pattern of the diffraction component may correspond to the pattern of the content displayed on the inner surface of the gantry 910. For example, when the pattern of the diffraction component is an animal, the pattern of the content may be the animal. After the light beams generated by the light source passes through the corresponding diffraction component, the pattern may be projected into the bore 914, so that the bore 914 may have a certain brightness intensity while presenting the pattern inside, which may further relieve the panic and/or the anxiety of the patient. In some embodiments; the patterns of the diffraction components may be designed to adapt to different needs. For example, different diffraction components may correspond to different objects (e.g., children). As another example, the light beams of the two light sources 921 and 922 may be superimposed to produce a staggered pattern (e.g., a starry sky pattern) in the bore 914, thereby presenting a stereoscopic effect. As used herein, the starry sky pattern may include a series of irregular bright spots, which are caused by a difference in the diffraction effect of the diffraction component.

In some embodiments, the lighting device 920 may further include a LED strip 926 shown in FIG. 9B. The LED strip 926 may be configured to assist the light source 921 and/or the light source 922 to light the bore 914. The LED strip 926 may be set on the end of the sagittal axial of the gantry 920 where at least one of the light sources 921 and 922 is located. For example, the LED strip 926 may have good flexibility and be arranged on the edge of the bore 914 as shown in FIG. 9B. As another example, the entrance end of the bore 914 may include a horn-shaped entrance 912. The LED strip 926 may be arranged at a transition area between the horn-shaped entrance 912 and the inner surface of the gantry 910.

In some embodiments, a brightness intensity of the LED strip 926 may be kept constant. In some embodiments, a brightness intensity of the LED strip may change at a first frequency, and a brightness intensity of at least one of the light sources 921 and 922 may change at a second frequency. The first frequency may be the same as or different from the second frequency.

According to some embodiments of the present disclosure, when the couch moves the object (e.g., a patient) in the axial direction of the gantry 910 with a longer length, the object may be located in a dark, enclosed, and narrow environment. For a patient, especially those suffering from claustrophobia, the dark, enclosed, and narrow environment may make them panic and/or anxiety, which may cause the patient to move due to anxiety, thereby reducing the efficiency and/or accuracy of the medical treatment and/or imaging. As a result, by using the lighting device 920, the bore 914 may be in a bright environment when the patient is undergoing the medical treatment and/or imaging, which may relieve the panic and/or anxiety of the patient, thereby reducing the patient's movement (e.g., maintaining a predetermined lying position) due to anxiety and improving the efficiency and/or accuracy of the medical treatment or imaging.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the lighting device 920 may further include a support component 930 configured to support the one or more light sources and the one or more display apparatuses as shown in FIGS. 9B and 9C. More descriptions regarding the support component 930 may be found elsewhere in the present disclosure. See, e.g., FIGS. 9D and 9E and the relevant descriptions thereof. As another example, the lighting device 920 may be installed in some other devices with a bore that needs to be illuminated.

Figure 9D:
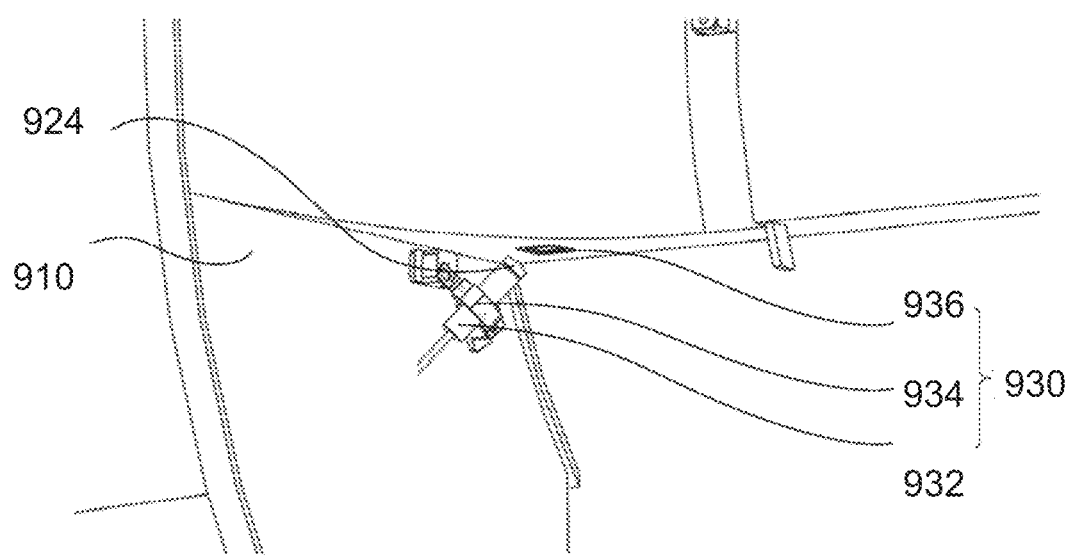
FIG. 9D is a partial enlarged view of a support component of a lighting device according to some embodiments of the present disclosure.
Figure 9E:
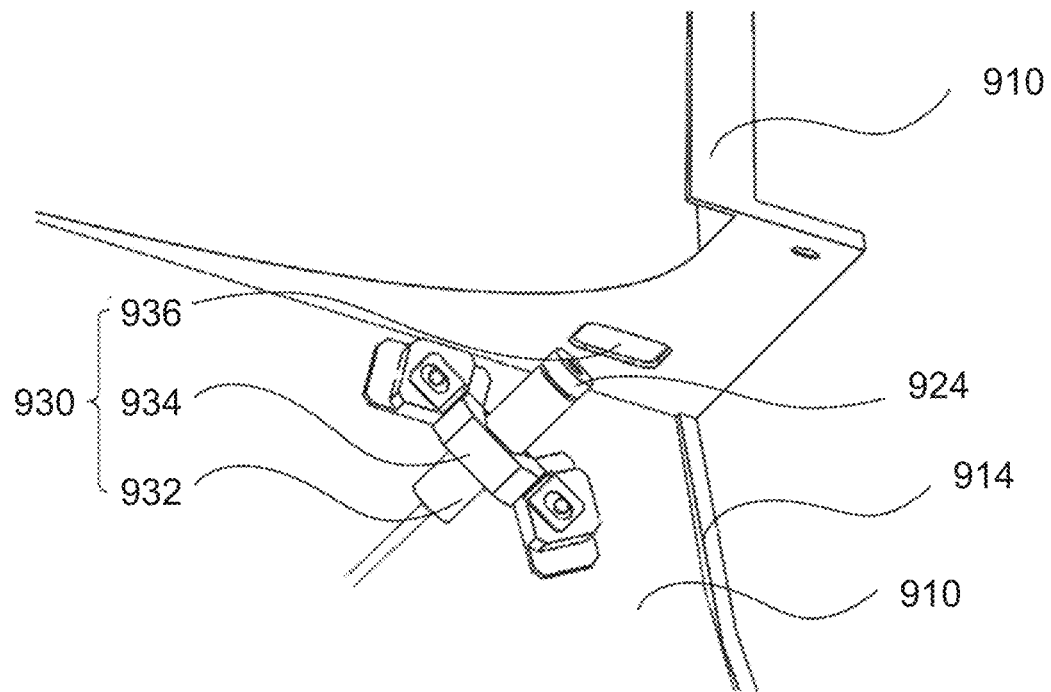
FIG. 9E is a partial enlarged view of a support component of a lighting device according to some embodiments of the present disclosure.

FIGS. 9D and 9E are partial enlarged views of a support component of a lighting device according to some embodiments of the present disclosure. The support component 930 as shown in FIG. 9C may be configured to support a light source (e.g., the light source 922) and the corresponding diffraction component (i.e., the display apparatus 924). As shown in FIGS. 9D and 9E, the support component 930 may include a support unit 932 and a mounting bracket 934.

The support unit 932 may be configured to support the light source (e.g., the light source 922) and the corresponding diffraction component (i.e., the display apparatus 924). In some embodiments, the support unit 932 may include a tube. The diffraction component (i.e., the display apparatus 924) may be arranged on an end of the tube. The light source may be movably arranged in the tube to adjust a focal length of the light source. In some embodiments, a cross-section of the tube may be a rectangle, a circle, a triangle, or, the like. A cross-sectional area of the tube may be within a threshold to avoid scattering of the light beams generated by the light source 922 when the light beams pass through the diffraction component (i.e., the display apparatus 924).

The mounting bracket 934 may be configured to support or mount the support unit 932. In some embodiments, the mounting bracket 934 may have a V-shape, a C-shape, etc. In some embodiments, the support component 930 may be provided independently of the gantry 910. In other words, the support component 930 may be separated from the gantry 910. For example, the mounting bracket 934 may be installed on the ground or on a mounting base that is near the end of the gantry 910 to ensure that the light beams generated by the light source 922 can be projected into the bore 914. Alternatively, the support component 930 may be installed in the gantry 910. For example, the support component 930 may be arranged at the entrance of the bore 914 and physically connected with the cover of the gantry 910. In some embodiments, the gantry 910 may include a transparent window 936 to allow the light beams to pass through and project into the bore 914. The two ends of the mounting bracket 934 may be fixedly connected on the gantry 910 by, for example, nuts, rivets, etc.

In some embodiments, the mounting bracket 934 may include a main body and two auxiliary parts. The main body may include a concave configured to accommodate the support unit 932 (e.g., a tube). The two auxiliary parts may be located at two sides of the main body. The two auxiliary parts may be physically connected with the gantry 910 to fix or mount the support unit 932.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the Ike, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A display apparatus, comprising:
a display panel including a frame area and a display area;
a display component configured to display a content including a target portion and a background portion on the display area;
an image acquisition device configured to acquire an image of the display panel, wherein the image includes a representation of at least one portion of the frame area and at least one portion of the display area; and
a control device configured to control the display component to adjust the background portion of the content displayed on the display area according to the image of the display panel to reduce a visual difference between the background portion of the content and the frame area of the display panel.

2. The display apparatus of claim 1, wherein to adjust the background portion of the content displayed on the display area according to the image of the display panel, the control device is further configured to:
  determine a reference value of an image parameter of the frame area represented in the image of the display panel;
  determine a value of the image parameter of the background portion represented in the image; and
  control the display component to adjust one or more display parameters of the background portion according to the value of the image parameter of the background portion and the reference value of the image parameter of the frame area.

3. The display apparatus of claim 2, wherein after adjusting the one or more display parameters of the background portion, a difference between the value of the image parameter of the background portion and the reference value of the image parameter of the frame area is smaller than a threshold.

4. The display apparatus of claim 2, wherein after adjusting the one or more display parameters of the background portion, the value of the image parameter of the background portion is the same as the reference value of the image parameter of the frame area.

5. The display apparatus of claim 2, wherein the control device is further configured to:
  determine a value of the image parameter of the target portion represented in the image; and
  adjust one or more display parameters of the target portion based on the value of the image parameter of the target portion and the reference value of the image parameter of the frame area.

6. The display apparatus of claim 2, wherein the image parameter includes at least one of a color parameter or a brightness parameter.

7. The display apparatus of claim 1, wherein the display component includes a light emitting element, the light emitting element includes at least one of a thin film transistor liquid crystal, an organic light-emitting diode (OLED), a LED dot matrix, a micro light emitting diode (micro LED) a plasma light emitting element, or a projector.

8. The display apparatus of claim 1, wherein
  the display component is located at a first side of the display panel or is spaced apart from the display panel; and
  the image acquisition device is located at the first side or a second side of the display panel, a field of view (FOV) of the image acquisition device covers the at least one portion of the frame area and the at least one portion of the display area.

9. The display apparatus of claim 1, wherein the display apparatus is arranged in a medical device including a gantry with a bore, wherein
  the display panel includes at least a portion of an inner surface of the gantry.

10. The display apparatus of claim 9, wherein the display component includes:
  one or more light sources configured to provide lighting for the bore; and
  one or more diffraction components configured to generate the content based on one or more light beams generated by the one or more light sources and display the content on the inner surface of the gantry, each diffraction component corresponding to one light source.

11. A method for borderless display, comprising:
  obtaining an image of a display panel of a display apparatus, the display panel including a display area and a frame area, a content including a target portion and a background portion being displayed on the display area, the image of the display panel including a representation of at least one portion of the frame area and at least one portion of the display area;
  determining a reference value of an image parameter of the frame area represented in the image of the display panel;
  determining a value of the image parameter of the background portion represented in the image; and
  adjusting one or more display parameters of the background portion according to the value of the image parameter of the background portion and the reference value of the image parameter of the frame area.

12. A medical device, comprising:
  a gantry including a bore configured to accommodate an object; and
  a lighting device including one or more light sources and one or more display apparatuses, wherein
    the one or more light sources are configured to provide lighting for the bore; and
    the one or more display apparatuses are configured to display a content on an inner surface of the gantry, wherein at least one of the one or more display apparatuses includes:
      a control device configured to adjust the content displayed on the inner surface of the gantry.

13. The medical device of claim 12, wherein the inner surface of the gantry includes a frame area and a display area, and the content including a target portion and a background portion on the display area, the at least one of the one or more display apparatuses further includes:
  an image acquisition device configured to acquire an image of the inner surface of the gantry, wherein the image includes at least a portion of the frame area and at least a portion of the display area; wherein
  the control device is further configured to adjust the background portion of the content displayed on the display area according to the image of the inner surface of the gantry.

14. The medical device of claim 12, wherein
  one of the one or more light sources is arranged at an end of a sagittal axial of the gantry; and
  one of the one or more display apparatuses includes a diffraction component configured to generate the content based on a light beam generated by the one of the one or more light sources and display the content on the inner surface of the gantry.

15. The medical device of claim 14, wherein
  one of the one or more light sources includes at least one of a laser light or a LED light; and
  the diffraction component includes a grating element.

16. The medical device of claim 14, wherein the lighting device further includes a LED strip, the LED strip being set on the end of the sagittal axial of the gantry where the one of the one or more light sources is located.

17. The medical device of claim 16, wherein a brightness intensity of the LED strip changes at a first frequency, and a brightness intensity of at least one of the one or more light sources changes at a second frequency, wherein the first frequency is same as the second frequency.

18. The medical device of claim 14, wherein the lighting device further includes:
  a support component configured to support the one of the one or more light sources and the diffraction component.

19. The medical device of claim 18, wherein the support component has a tube, wherein the diffraction component is arranged on an end of the tube, and one of the light sources is movably arranged in the support component to adjust a focal length of the one of the light sources.

20. The medical device of claim 14, wherein the diffraction component includes a pattern configured to provide the content for display, and the pattern includes at least one of a geometric pattern, an animal pattern, a constellation pattern, a letter, or a number.

* * * * *